United States Patent
Flanagan et al.

(10) Patent No.: US 11,963,862 B2
(45) Date of Patent: Apr. 23, 2024

(54) CELL ENCAPSULATION DEVICE INCLUDING A POROUS TUBE

(71) Applicant: Boston Scientific Scimed Inc., Maple Grove, MN (US)

(72) Inventors: Aiden Flanagan, Kilcolgan (IE); Matthew McEvaddy, Galway (IE); Martin L. Fawdry, Galway (IE)

(73) Assignee: Boston Scientific Scimed, Inc., Maple Grove, MN (US)

(*) Notice: Subject to any disclaimer, the term of this patent is extended or adjusted under 35 U.S.C. 154(b) by 991 days.

(21) Appl. No.: 16/546,951

(22) Filed: Aug. 21, 2019

(65) Prior Publication Data

US 2020/0060804 A1 Feb. 27, 2020

Related U.S. Application Data

(60) Provisional application No. 62/721,063, filed on Aug. 22, 2018.

(51) Int. Cl.
*A61F 2/02* (2006.01)
*A61L 31/14* (2006.01)
(Continued)

(52) U.S. Cl.
CPC ............ *A61F 2/022* (2013.01); *A61L 31/146* (2013.01); *A61L 31/16* (2013.01); *A61M 31/002* (2013.01);
(Continued)

(58) Field of Classification Search
CPC .. A61F 2/06; A61F 2/22; A61M 5/178; A61N 1/05; A61K 49/00; A61L 31/146
See application file for complete search history.

(56) References Cited

U.S. PATENT DOCUMENTS 4,723,953 A 2/1988 Rosenbaum et al.
5,262,055 A 11/1993 Bae et al.
(Continued)

FOREIGN PATENT DOCUMENTS

CN 1373679 A 10/2002
CN 105813630 A 7/2016
(Continued)

OTHER PUBLICATIONS

International Preliminary Report on Patentabilty issued in PCT/EP2018/057053, dated Oct. 3, 2019, 8 pages.
(Continued)

*Primary Examiner* — Dah-Wei D. Yuan
*Assistant Examiner* — Andrew J Bowman
(74) *Attorney, Agent, or Firm* — Seager, Tufte & Wickhem, LLP

(57) ABSTRACT

A cell encapsulation device for implantation in a body includes one or more cell encapsulation layers, each of the one or more cell encapsulation layers including at least one membrane and a guide tube. The at least one membrane is semipermeable. The least one membrane forms a chamber for encapsulating cells and at least one access port through the at least one membrane. The guide tube extends into the chamber from the at least one access port. The guide tube includes a porous wall along at least a portion of its length. The guide tube is capable of guiding movement of a catheter within the chamber.

10 Claims, 5 Drawing Sheets

(51) Int. Cl.
    *A61L 31/16*      (2006.01)
    *A61M 31/00*      (2006.01)
    *A61M 39/02*      (2006.01)
    *C12N 5/071*      (2010.01)

(52) U.S. Cl.
    CPC .... *A61M 39/0208* (2013.01); *A61M 39/0247* (2013.01); *A61L 31/148* (2013.01); *A61M 2039/0282* (2013.01); *C12N 5/0677* (2013.01)

(56) References Cited

U.S. PATENT DOCUMENTS

| | | | |
|---|---|---|---|
| 5,324,518 A | 6/1994 | Orth et al. | |
| 5,964,804 A | 10/1999 | Brauker et al. | |
| 8,444,630 B2 | 5/2013 | Rotem et al. | |
| 9,011,899 B2 | 4/2015 | Hasilo et al. | |
| 9,084,870 B2 | 7/2015 | Deniega et al. | |
| 9,132,226 B2 | 9/2015 | Martinson et al. | |
| 10,668,106 B2 | 6/2020 | Bou Aoun et al. | |
| 2004/0067540 A1* | 4/2004 | Lassota | A61K 49/0004 435/7.23 |
| 2006/0247750 A1* | 11/2006 | Seifert | A61N 1/056 607/122 |
| 2008/0015674 A1* | 1/2008 | Austin | A61F 2/95 623/1.11 |
| 2009/0018033 A1 | 1/2009 | Morgan et al. | |
| 2009/0054826 A1 | 2/2009 | Hoffa | |
| 2010/0121446 A1 | 5/2010 | Bruce et al. | |
| 2010/0124564 A1 | 5/2010 | Martinson et al. | |
| 2010/0209468 A1 | 8/2010 | Kennedy et al. | |
| 2014/0154299 A1 | 6/2014 | Ortiz-Austin et al. | |
| 2014/0257515 A1 | 9/2014 | So et al. | |
| 2015/0112247 A1* | 4/2015 | Tempelman | A61F 2/022 435/283.1 |
| 2016/0235902 A1 | 8/2016 | Flanagan et al. | |
| 2016/0250262 A1 | 9/2016 | Agulnick et al. | |
| 2017/0105832 A1 | 4/2017 | Rosenblum | |
| 2018/0125632 A1 | 5/2018 | Cully et al. | |
| 2018/0263238 A1 | 9/2018 | Flanagan et al. | |

FOREIGN PATENT DOCUMENTS

| | | |
|---|---|---|
| EP | 2595567 A1 | 5/2013 |
| WO | 1991000119 A1 | 1/1991 |
| WO | 2010057039 A2 | 5/2010 |
| WO | 2012010767 A1 | 1/2012 |
| WO | 2020/041446 A1 | 2/2020 |

OTHER PUBLICATIONS

International Search Report and Written Opinion issued in PCT/EP2018/057053, dated Jun. 18, 2018, 12 pages.

Johnson, Amy S.; et al. "Quantitative Assessment of Islets of Langerhans Encapsulated in Alginate." Tissue Engineering: Part C, 17(4):435-449, 2011.

Khattak, Sarwat F. et al. "Enhancing Oxygen Tension and Cellular Function in Alginate Cell Encapsulation Devices Through the Use of Perfluorocarbons." Biotechnology and Bioengineering, 96(1):156-166, Jan. 1, 2007.

Communication Relating to the Results of the Partial International Search and Provisional Opinion issued in PCT/US2019/047468, dated Dec. 16, 2019, 7 pages.

\* cited by examiner

CELL ENCAPSULATION DEVICE INCLUDING A POROUS TUBE

CROSS REFERENCE TO RELATED APPLICATION

This application claims priority to Provisional Application No. 62/721,063, filed Aug. 22, 2018, which is herein incorporated by reference in its entirety.

TECHNICAL FIELD

The present disclosure relates to implantable medical devices and methods for the encapsulation of cells. More specifically, the disclosure relates to implantable devices and methods for accessing encapsulating insulin-producing cells.

BACKGROUND

Implantable medical devices using encapsulation of insulin-producing cells to treat diabetes may suffer from several issues. One issue is lack of robustness of the devices stemming from an inability to provide sufficient cell sustaining materials, such as oxygen and nutrients, to keep the insulin-producing cells not only alive, but healthy enough to produce insulin. Other issues include the difficulties, traumas, and inherent risks that may be associated with the surgery required to implant encapsulation devices.

Improvements are needed in implantable devices for encapsulating cells that reduce the risks that may be associated with the surgery required to implant encapsulation devices, and to improve the robustness of such devices.

SUMMARY

Example 1 is a cell encapsulation device for implantation in a body. The cell encapsulation device includes one or more cell encapsulation layers, each of the one or more cell encapsulation layers including at least one membrane and a guide tube. The at least one membrane is semipermeable. The least one membrane forms a chamber for encapsulating cells and at least one access port through the at least one membrane. The guide tube extends into the chamber from the at least one access port. The guide tube includes a porous wall along at least a portion of its length. The guide tube is capable of guiding movement of a catheter within the chamber.

Example 2 is the cell encapsulation device of Example 1, wherein the at least one membrane includes a first membrane and a second membrane. Each of the one or more cell encapsulation layers further includes a first plurality of weld lines. The second membrane is attached to the first membrane by the first plurality of weld lines. The first membrane, the second membrane, and the first plurality of weld lines define the chamber.

Example 3 is the cell encapsulation device of either of Examples 1 or 2, wherein the guide tube is formed at least in part of a metal mesh.

Example 4 is the cell encapsulation device of any of Examples 1-3, wherein each of the cell encapsulation layers further includes a second plurality of weld lines defining at least two cell channels within the chamber, and a third plurality of weld lines defining a guide tube channel in fluid communication with the at least two cell channels. The guide tube is contained within the guide tube channel.

Example 5 is the cell encapsulation device of any of Examples 1-4, further including at least one access catheter extending away from the chamber from the at least one access port. The at least one access catheter is fluidly connected to the guide tube.

Example 6 is the cell encapsulation device of Example 5, wherein the at least one access port includes a first access port and a second access port. The at least one access catheter includes a first access catheter fluidly connected the first access port, and a second access catheter fluidly connected to the second access port. The guide tube extends through the chamber from the first access port to the second access port.

Example 7 is the cell encapsulation device of Example 6, wherein the one or more cell encapsulation layers includes a first cell encapsulation layer and a second cell encapsulation layer. The second access catheter of the first cell encapsulation layer is fluidly connected to the first access catheter of the second cell encapsulation layer to fluidly connect the first cell encapsulation layer to the second cell encapsulation layer.

Example 8 is the cell encapsulation device of any of Examples 5-7, wherein the cell encapsulation device further includes an injection port connected to an end of an access catheter opposite the chamber, the injection port including a port housing, an outer septum, and an inner septum. The port housing forms a port lumen extending through the port housing. An end of the port housing nearest the access catheter is in fluid communication with the access catheter. The outer septum extends across and seals the port lumen. The inner septum extends across and seals the port lumen. The inner septum is spaced apart from the outer septum to form a space within the port lumen and between the inner septum and the outer septum. The inner septum is disposed between the outer septum and the access catheter. The outer septum and the inner septum are formed of a resilient polymer.

Example 9 is a system for cell implantation in a body. The system includes the cell encapsulation device according to any of Examples 5-8 and a first external catheter capable of passing through the at least one access catheter and into the guide tube to guide movement of the first external catheter within the chamber.

Example 10 is the system of Example 9, wherein the first external catheter is capable of dispense cells through the porous wall of the guide tube and into the chamber as the first external catheter moves through the guide tube.

Example 11 is the system of Example 9, wherein the first external catheter includes a first lumen including a first lumen opening and a second lumen including a second lumen opening. The first lumen opening and the second lumen opening are spaced apart from each other along the guide tube. The first lumen opening is capable of dispensing a fluid through the porous wall of the guide tube and into the chamber. The second lumen opening capable of extracting the fluid from the chamber through the porous wall of the guide tube.

Example 12 is the system of Example 11, wherein the second lumen is disposed coaxially with the first lumen. The first external catheter further includes a flange disposed between the first lumen opening and the second lumen opening. The flange projects outward toward the guide tube to deflect fluid dispensed from the first lumen toward the porous wall of the guide tube.

Example 13 is the system of Example 9, wherein the first external catheter includes a first lumen and the first external catheter is capable of passing through the first access catheter and into the guide tube. The system further includes a second external catheter including a second lumen. The second external catheter is capable of passing through the second access catheter and into the guide tube opposite the first external catheter. The first external catheter and the second external catheter are spaced apart from each other within the chamber. The first external catheter is capable of dispensing a fluid through the porous wall of the guide tube and into the chamber. The second external catheter is capable of extracting the fluid from the chamber through the porous wall of the guide tube.

Example 14 is the system of Example 9, wherein the at least one access port includes a first access port and a second access port. The at least one access catheter includes a first access catheter fluidly connected the first access port, and a second access catheter fluidly connected to the second access port. The guide tube extends through the chamber from the first access port to the second access port. The first external catheter is capable of passing into the chamber through the first access catheter, through the guide tube, and out of the chamber through the second access catheter.

Example 15 is a method for making a cell encapsulation device for implantation in a body. The method includes placing a first semipermeable membrane directly on a second semipermeable membrane; attaching the first semipermeable membrane to the second semipermeable membrane with first plurality of weld lines defining a chamber for encapsulating cells, a second plurality of weld lines to define at least two cell channels within the chamber, and a third plurality of weld lines defining a guide tube channel in fluid communication with the at least two cell channels; inserting a guide tube into the guide tube channel through an access port into the chamber, the guide tube including a porous wall along at least a portion of its length; and attaching an end of the guide tube to at least one of: the first semipermeable membrane and the second semipermeable membrane surrounding the access port.

Example 16 is a cell encapsulation device for implantation in a body. The cell encapsulation device includes one or more cell encapsulation layers, each of the cell encapsulation layers including a first membrane that is semipermeable, a second membrane that is semipermeable, a first plurality of weld lines, and a guide tube. The second membrane is attached to the first membrane by the first plurality of weld lines. The first membrane, the second membrane, and the first plurality of weld lines define a chamber for encapsulating cells. The chamber includes at least one access port. The guide tube extends into the chamber from the at least one access port. The guide tube includes a porous wall along at least a portion of its length. The guide tube is capable of guiding movement of a catheter within the chamber.

Example 17 is the cell encapsulation device of Example 16, wherein the guide tube includes a metal mesh.

Example 18 is the cell encapsulation device of Example 17, wherein the metal mesh includes a metal selected from the group consisting of: stainless steel, titanium, platinum, an alloy of chromium and cobalt, an alloy of nickel and titanium, and an alloy of cobalt, chromium, nickel, and molybdenum.

Example 19 is the cell encapsulation of Example 16, wherein each of the cell encapsulation layers further includes a second plurality of weld lines defining at least two cell channels within the chamber and a third plurality of weld lines defining a guide tube channel in fluid communication with the at least two cell channels. The guide tube is contained within the guide tube channel.

Example 20 is the cell encapsulation device of Example 16, further including at least one access catheter extending away from the chamber from the at least one access port, the at least one access catheter fluidly connected to the guide tube.

Example 21 is the cell encapsulation device of Example 20, wherein the at least one access port includes a first access port and a second access port. The at least one access catheter includes a first access catheter fluidly connected the first access port, and a second access catheter fluidly connected to the second access port. The guide tube extends through the chamber from the first access port to the second access port.

Example 22 is the cell encapsulation device of Example 21, wherein the one or more cell encapsulation layers includes a first cell encapsulation layer and a second cell encapsulation layer. The second access catheter of the first cell encapsulation layer is fluidly connected to the first access catheter of the second cell encapsulation layer to fluidly connect the first cell encapsulation layer to the second cell encapsulation layer.

Example 23 is the cell encapsulation device of Example 20, wherein the cell encapsulation device further includes an injection port fluidly connected to an end of the at least one access catheter opposite the chamber. The injection port includes a port housing, an outer septum, and an inner septum. The port housing forms a port lumen extending through the port housing. An end of the port housing nearest the access catheter is in fluid communication with the access catheter. The outer septum extends across the port lumen and seals the port lumen. The inner septum extends across the port lumen and seals the port lumen. The inner septum is spaced apart from the outer septum to form a space within the port lumen and between the inner septum and the outer septum. The inner septum is disposed between the outer septum and the access catheter. The outer septum and the inner septum are formed of a resilient polymer.

Example 24 is a system for cell implantation in a body. The system includes a cell encapsulation device and at least one access catheter. The cell encapsulation device includes one or more cell encapsulation layers, each of the cell encapsulation layers including a first membrane that is semipermeable, a second membrane that is semipermeable, a first plurality of weld lines, and a guide tube. The second membrane is attached to the first membrane by the first plurality of weld lines. The first membrane, the second membrane, and the first plurality of weld lines define a chamber for encapsulating cells. The chamber includes at least one access port. The guide tube extends into the chamber from the at least one access port. The guide tube includes a porous wall along at least a portion of its length. The at least one access catheter extends away from the chamber from the at least one access port. The at least one access catheter is fluidly connected to the guide tube. The first external catheter is capable of passing through the at least one access catheter and into the guide tube. The guide tube is capable of guiding movement of the first external catheter within the chamber.

Example 25 is the system of Example 24, wherein the first external catheter is capable of dispensing cells through the porous wall of the guide tube and into the chamber as the first external catheter moves through the guide tube.

Example 26 is the system of Example 24, wherein the first external catheter includes a first lumen including a first lumen opening and a second lumen including a second lumen opening. The first lumen opening and the second lumen opening are spaced apart from each other along the guide tube. The first lumen opening is capable of dispensing a fluid through the porous wall of the guide tube and into the chamber. The second lumen opening is capable of extracting the fluid from the chamber through the porous wall of the guide tube.

Example 27 is the system of Example 26, wherein the second lumen is disposed coaxially with the first lumen. The first external catheter further includes a flange disposed between the first lumen opening and the second lumen opening. The flange projects outward toward the guide tube to deflect fluid dispensed from the first lumen toward the porous wall of the guide tube.

Example 28 is the system of Example 24, further including a second external catheter including a second lumen. The first external catheter includes a first lumen. The at least one access port includes a first access port and a second access port. The guide tube extends through the chamber from the first access port to the second access port. The at least one access catheter includes a first access catheter fluidly connected the first access port, and a second access catheter fluidly connected to the second access port. The first external catheter is capable of passing through the first access catheter and into the guide tube. The second external catheter is capable of passing through the second access catheter and into the guide tube opposite the first external catheter. The first external catheter and the second external catheter are spaced apart from each other within the chamber. The first external catheter is capable of dispersing a fluid through the porous wall of the guide tube and into the chamber. The second external catheter is capable of extracting the fluid from the chamber through the porous wall of the guide tube.

Example 29 is the system of Example 28, further including a guide wire extending through the first lumen and the second lumen. The guide wire includes a flange projecting toward the guide tube between the first external catheter and the second external catheter to deflect fluid dispensed from the first external catheter toward the porous wall of the guide tube.

Example 30 is the system of Example 24, wherein the at least one access port includes a first access port and a second access port. The at least one access catheter includes a first access catheter fluidly connected to the first access port and a second access catheter fluidly connected to the second access port. The guide tube extends through the chamber from the first access port to the second access port. The first external catheter is capable of passing into the chamber through the first access catheter, through the guide tube, and out of the chamber through the second access catheter.

Example 31 includes the system of Example 24, wherein the cell encapsulation device further includes an injection port fluidly connected to an end of the at least one access catheter opposite the chamber. The injection port includes a port housing, an outer septum, and an inner septum. The port housing forming a port lumen extending through the port housing. An end of the port housing nearest the access catheter is in fluid communication with the access catheter. The outer septum extends across the port lumen and seals the port lumen. The inner septum extends across the port lumen and seals the port lumen. The inner septum spaced is apart from the outer septum to form a space within the port lumen and between the inner septum and the outer septum. The inner septum is disposed between the outer septum and the access catheter. The outer septum and the inner septum are formed of a resilient polymer.

Example 32 is the system of Example 31, further including an outer tubular needle and an inner tubular needle. The outer tubular needle is capable of penetrating the outer septum. The outer septum is capable of sealing around the outer tubular needle. The inner tubular needle is capable of passing through the outer tubular needle and penetrating the inner septum. The inner septum is capable of sealing around the inner tubular needle. The first external catheter is capable of passing through the inner tubular needle, the at least one access catheter, and into the guide tube.

Example 33 is method for making a cell encapsulation device for implantation in a body. The method includes placing a first semipermeable membrane directly on a second semipermeable membrane; attaching the first semipermeable membrane to the second semipermeable membrane with a first plurality of weld lines defining a chamber for encapsulating cells; inserting a guide tube into the chamber through a first access port into the chamber, the guide tube including a porous wall along at least a portion of its length; and attaching an end of the guide tube to at least one of: the first semipermeable membrane and the second semipermeable membrane surrounding the first access port.

Example 34 is the method of Example 33, wherein attaching the first semipermeable membrane to the second semipermeable membrane further includes with a second plurality of weld lines defining at least two cell channels within the chamber, and with a third plurality of weld lines defining a guide tube channel in fluid communication with the at least two cell channels; and further including inserting the guide tube into the chamber includes inserting the guide tube into the guide tube channel through the first access port into the chamber.

Example 35 is the method of Example 33, further including attaching an end of the guide tube opposite the end of the guide tube attached to at least one of: the first semipermeable membrane and the second semipermeable membrane surrounding the first access port, to at least one of: the first semipermeable membrane and the second semipermeable membrane surrounding a second access port into the chamber.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
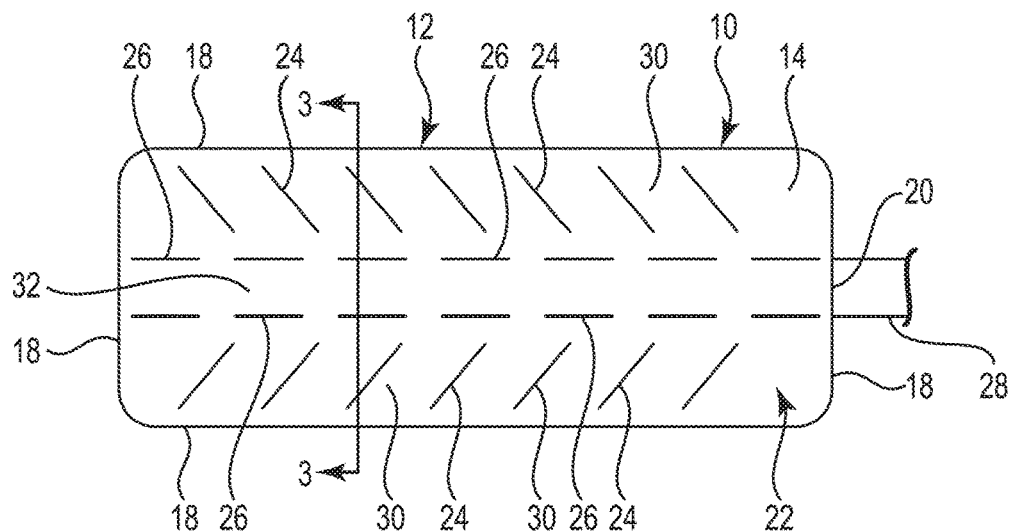
FIG. 1 is a schematic top view of a cell encapsulation device, according to some embodiments of this disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosed subject matter as defined by the appended claims.

DETAILED DESCRIPTION

Devices according to this disclosure include an implantable device for encapsulating cells. The cell encapsulation devices may promote the oxygen and nutrient flow to the encapsulated cells while isolating the cells from a patient's immune system. Once implanted, the cell encapsulation devices may be filled with insulin-producing cells. In time, should the insulin-producing cells need to be replenished, the cell encapsulation devices may be cleaned and refilled in a minimally invasive fashion to reduce the trauma experienced by the patient.

FIG. 1 is a schematic top view of a cell encapsulation device 10 according to some embodiments of this disclosure. As shown in FIG. 1, a cell encapsulation device 10 includes at least one cell encapsulation layer 12. The cell encapsulation layer 12 includes a first membrane 14, a second membrane 16 (shown in FIG. 2), a first plurality of weld lines 18, and a first access port 20. The first plurality of weld lines 18 attaches the first membrane 14 to the second membrane 16. The first membrane 14, the second membrane 16, and the first plurality of weld lines 18 define at least one chamber 22.

As shown in FIG. 1, the cell encapsulation device 10 may further include a second plurality of weld lines 24, a third plurality of weld lines 26, and a first access catheter 28. The second plurality of weld lines 24 attaches the first membrane 14 to the second membrane 16 to define at least two cell channels 30 of the chamber 22. The third plurality of weld lines 26 attaches the first membrane 14 to the second membrane 16 to define a guide tube channel 32 within the chamber 22.

The first access catheter 28 is fluidly connected to the guide tube 34 and extends away from the chamber 22 from the first access port 20. The first access catheter 28 may be a tubular structure formed of a biocompatible polymer, for example, high-density polyethylene, polyethylene terephthalate, or polytetrafluoroethylene; or a biocompatible metal, for example, 316 VLM stainless steel, Nitinol, or Elgiloy®. The first access catheter 28 may be attached to the first membrane 14 and/or the second membrane 16 by, for example, welding to the first membrane 14 and/or the second membrane 16, or with a biocompatible adhesive.

The first membrane 14 and the second membrane 16 are semipermeable membranes having pores extending through the membranes. The first membrane 14 and the second membrane 16 are semipermeable in that the pores are sized to permit the passage of oxygen, nutrients, and waste products to pass through, but prevent the passage of encapsulated cells or cells of the patient's immune system.

The first membrane 14 and the second membrane 16 may have an average pore diameter as small as 2 nanometers (nm), 5 nm, 10 nm, or 20 nm, or 50 nm, or as large as 200 nm, 500 nm, 1,000 nm, 2,000 nm, or 5,000 nm, or within any range defined by any two of the foregoing values. The average pore diameter may range from 2 nm to 5,000 nm, 5 nm to 2,000 nm, 10 nm to 1,000 nm, 20 nm to 500 nm, or 50 nm to 200 nm. A pore diameter of 2 nm is sufficient to permit the passage of insulin and glucose through the first membrane 14 and the second membrane 16. A pore diameter less than 5,000 nm is sufficient to prevent vascularization and immune response within the cell channel 30.

The first membrane 14 and the second membrane 16 may be woven membranes, such as those available from Sefar AG Hinterbissaustrasse 12, 9410 Heiden, Switzerland. Additionally or alternatively, the first membrane 14 and the second membrane 16 may be non-woven membranes produced by electrospinning.

Figure 2:
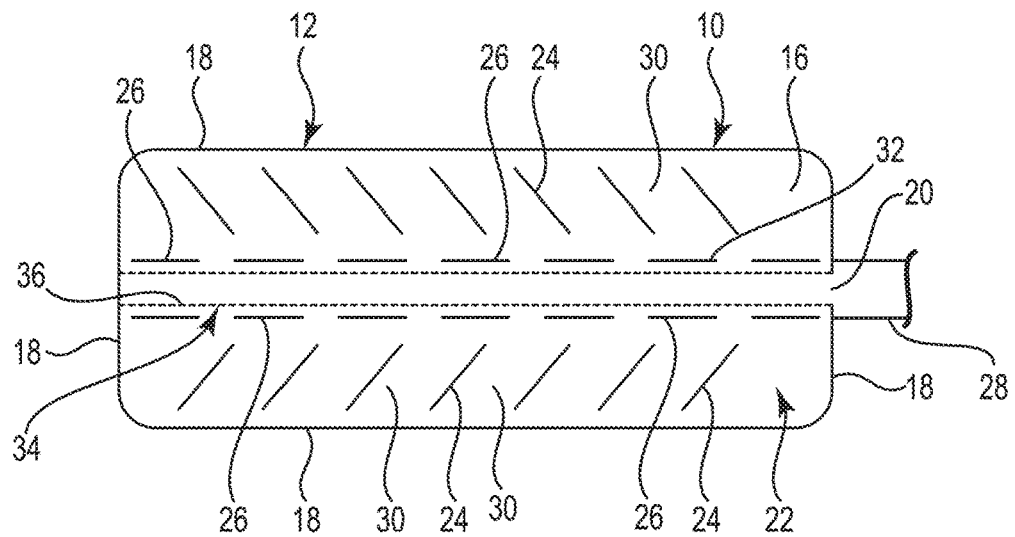
FIG. 2 is a schematic sectional top view of a cell encapsulation layer of the cell encapsulation device of FIG. 1, according to some embodiments of this disclosure.

FIG. 2 is a schematic sectional top view of the cell encapsulation layer 12 of FIG. 1 with the first membrane 14 removed such that the second membrane 16 is shown. As shown in FIG. 2, the cell encapsulation layer 12 further includes a guide tube 34 extending into the chamber 22 from the first access port 20. The guide tube 34 includes a porous wall 36 along at least a portion of its length. In the embodiment shown in FIG. 2, the porous wall 36 of the guide tube 34 extends the full length of the guide tube 34. Alternatively, the porous wall 36 extends along only one or more portions of the guide tube 34. The porous wall 36 permits fluids, gels, and encapsulated fluids to flow easily between the guide tube 34 and the cell channels 30. The guide tube 34 may be contained within the guide tube channel 32 to maintain the guide tube 34 in a position from which it may be fluidly connected to the cell channels 30.

The guide tube 34 may include a mesh pattern, such as a braided mesh, or a slotted mesh pattern as used for implantable stents, to form the porous wall 36. The guide tube 34 may include of a metal mesh. The metal mesh may include a metal selected from the group consisting of: stainless steel, titanium, platinum, an alloy of chromium and cobalt, an alloy of nickel and titanium, and an alloy of cobalt, chromium, nickel, and molybdenum. The guide tube 34 may include a polymer mesh. The polymer mesh may include a polymer selected from the group consisting of polytetrafluoroethylene, polyether block amide, nylon, polyester, polysiloxane, and polycarbonate polyurethane.

Holes or openings of the mesh may provide pores through the porous wall 36. The pores in the porous wall 36 may have an average pore diameter as small as 0.1 millimeters (mm), 0.2 mm, 0.3 mm, 0.4 mm, 0.6 mm, 0.8 mm, or 1.0 mm, or as large as 1.2 mm, 1.5 mm, 2 mm, 2.5 mm, 3 mm, 4 mm, or 5 mm, or within any range defined by any two of the foregoing values, such as 0.1 mm to 5 mm, 0.2 mm to 4 mm, 0.3 mm to 3 mm, 0.4 mm to 2.5 mm, 0.6 mm to 2 mm, 0.8 mm to 1.5 mm, 0.6 to 1.0, or 0.8 mm to 1.2 mm, for example.

Figure 3:
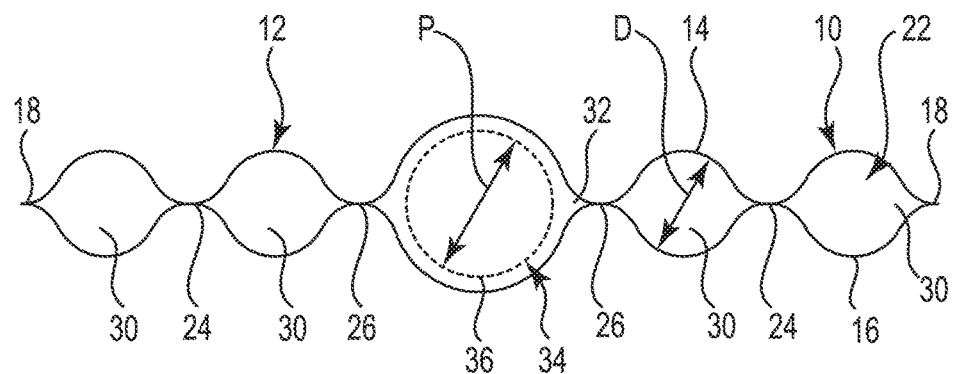
FIG. 3 is a schematic cross-sectional view of the cell encapsulation layer of the cell encapsulation device of FIG. 1, according to some embodiments of this disclosure.

FIG. 3 is a schematic cross-sectional view of the cell encapsulation layer 12 of FIG. 1 according to some embodiments of this disclosure. As shown in FIG. 3, the guide tube 34 may have an inside diameter P as small as 0.5 mm, 0.6 mm, 0.8 mm, 1.0 mm, 1.2 mm, 1.4 mm, or 1.6 mm, or as large as 1.8 mm, 2.0 mm, 2.2 mm, 2.4 mm, 2.6 mm, 2.8 mm, or 3.0 mm, or within any range defined by any two of the foregoing values, such as 0.5 mm to 3.0 mm, 0.6 mm to 2.8 mm, 0.8 mm to 2.6 mm, 1.0 mm to 2.4 mm, 1.2 mm to 2.2 mm, 1.4 mm to 2.0 mm, 1.6 mm to 1.8 mm, or 0.8 mm to 1.2 mm, for example.

The cell channels 30 may each have an average inside diameter D as small as 0.01 millimeters (mm), 0.02 mm, 0.04 mm, 0.06 mm, 0.08 mm, 0.10 mm, 0.12 mm, 0.16 mm, 0.2 mm, 0.4 mm, 0.6 mm, 0.8 mm, 1.0 mm, 1.2 mm, 1.6 mm, 2.0 mm, 2.4 mm, 2.8 mm, 3.2 mm, or 3.6 mm, or within any range defined by any two of the foregoing values, such as 0.01 mm to 3.6 mm, 0.1 mm to 2.0 mm, or 0.01 mm to 1.2 mm, for example.

As implanted, the cell channels 30 of the cell encapsulation device 10 may be uninflated, that is, they may not be filled with a fluid or insulin-producing cells, prior to implantation to enable implantation in a minimally invasive manner, as described in U.S. patent application Ser. No. 15/922, 251, entitled "Cell Encapsulation Device", filed Mar. 15, 2018, hereby incorporated by reference in its entirety. The cell encapsulation device 10 may be implanted in the patient's lower abdomen, for example, between the transversalis fascia and the Parietal peritoneum. Alternatively, the cell encapsulation device 10 may be implanted between the internal oblique muscle and the transversus abdominis muscle.

Considering FIGS. 1-3 together, a method for making a cell encapsulation device, such as the cell encapsulation device 10 for example, according to some embodiments, may include placing the first membrane 14 directly on the second membrane 16, and then attaching the first membrane 14 to the second membrane 16 with the first plurality of weld lines 18 to define the chamber 22 and a second plurality of weld lines 24 to define at least two cell channels 30 within the chamber 22. The guide tube 34 may be inserted into the chamber 22 through the first access port 20 and an end of the guide tube 34 may be attached to the first membrane 14 and/or the second membrane 16 surrounding the first access port 20. The second plurality of weld lines 24 may be omitted.

Attaching the first membrane 14 to the second membrane 16 may further include a third plurality of weld lines 26 defining the guide tube channel 32 in fluid communication with the cell channels 30. The method may further include inserting the guide tube 34 into the guide tube channel 32 through the first access port 20. The third plurality of weld lines 26 may be omitted.

Figure 4A:
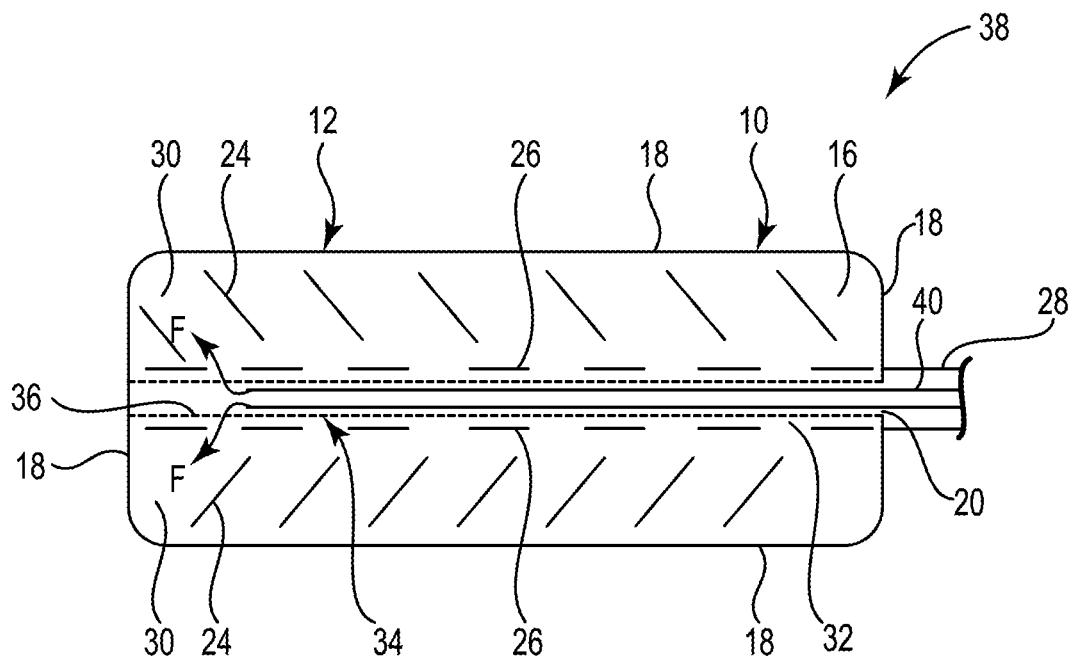
FIGS. 4A and 4B are schematic sectional top views of a system for cell implantation, according to some embodiments of this disclosure.
Figure 4B:
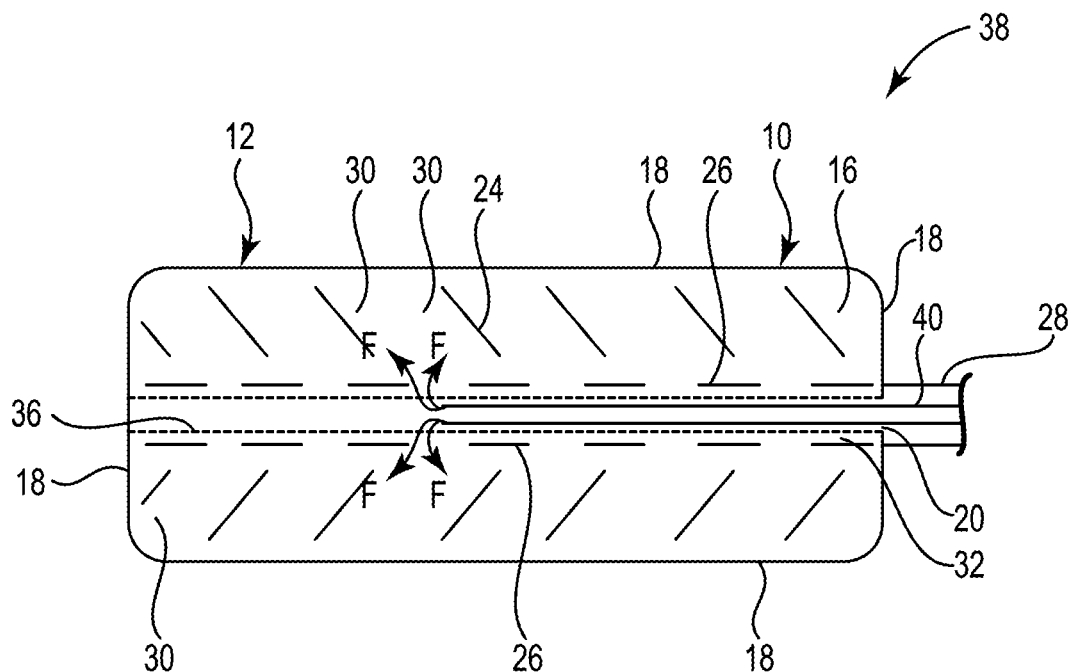

FIGS. 4A and 4B are schematic sectional top views of a system 38 for cell implantation including the cell encapsulation device 10 and a first external catheter 40. FIGS. 4A and 4B are shown with the first membrane 14 removed such that the second membrane 16 is shown for clarity. FIGS. 4A and 4B illustrate a method of filling of the cell encapsulation layer 12 of the cell encapsulation device 10 with the first external catheter 40 to inflate the cell channels 30 after implantation, according to some embodiments.

FIGS. 4A and 4B show the cell encapsulation layer 12 with the first external catheter 40 passing through the first access catheter 28, the first access port 20, and into the guide tube 34. The first external catheter 40 may be a simple catheter with an opening at its distal end and connected to, for example, a source of fluid or insulin-producing cells outside the patient (not shown). As shown in FIG. 4A, the first external catheter 40 may be inserted nearly to and end of the guide tube 34 away from the first access port 20, and then a flow F of fluid and/or insulin-producing cells may be injected into the chamber 22, flowing through the porous wall 36 of the guide tube 34 and into adjacent cell channels 30, filling the adjacent cell channels 30.

As the cell channels 30 farthest from the first access port 20 fill, the first external catheter 40 may be retracted toward the first access port 20 and continue to fill more of the cell channels 30 closer to the first access port 20, as shown in FIG. 4B. The first external catheter 40 may be retracted to the first access port 20 to fill the remaining cell channels 30 and complete filling of the cell encapsulation layer 12 with fluid and/or insulin-producing cells.

The guide tube 34 may guide the first external catheter 40 through the chamber 22 to help position the first external catheter 40 in a desired position for filling the chamber 22 in a controlled fashion, as described above. The guide tube 34 may prevent the first external catheter 40 from moving in an uncontrolled fashion within the chamber 22, which could lead to underfilling or overfilling some of the cell channels 30. In addition, the guide tube 34 may also prevent the first external catheter 40 from veering into the cell channels 30 and possibly damaging or puncturing the first membrane 14 or the second membrane 16.

The cell encapsulation device 10 may be implanted and immediately filed with insulin-producing cells, as described above. Alternatively, the cell encapsulation device 10 may be implanted and immediately filled with a fluid to inflate the cell channels 30. The cell encapsulation device 10 may then remain implanted in the inflated configuration to permit vasculature (not shown) from the patient to grow around the cell encapsulation device 10. Once the vasculature has grown enough to be able to supply oxygen and nutrients to the cell encapsulation device 10, the inflation fluid may be replaced with insulin-producing cells. The fluid used to inflate the cell channels 30 may include a saline solution. The fluid used to inflate the cell channels 30 may include a more viscous fluid, such as native hyaluronic acid. The fluid may remain in the cell channels 30 to keep the cell encapsulation device 10 in the inflated configuration. The more viscous fluid, such as the native hyaluronic acid, may remain in the cell channel 30 longer than, for example saline. This may provide additional time for the vasculature to grow before the insulin-producing cells are injected.

The insulin-producing cells may be injected in a gel matrix. The gel matrix may restrain movement of the insulin-producing cells so that they won't clump together. Such clumping together may reduce the number of the insulin-producing cells available to receive sustaining materials and produce insulin. The gel matrix may include a cross-linked hyaluronic acid and/or an alginate gel. The gel matrix may further include an emulsion including an oxygen-containing fluid. The high oxygen solubility of the oxygen-containing fluid may allow the distance D of the cell channels 30 (FIG. 3) to be greater than those in which the gel matrix does not include the emulsion including the oxygen-containing fluid. The oxygen-containing fluid may be, for example, a type of perfluorocarbon liquid, as is known in the art. Examples of such perfluorocarbon liquids may include perfluorodihexyl ether, perfluorodibutyl sulfur tetrafluoride, perfluorotriisobutylamine, perfluoro-(N-ethylmorpholine), perfluoro-N,N-dipropylmethylamine, perfluorotriethylamine, perfluoro-N-methylpiperidine, perfluoro-N-methylmorpholine, perfluoro-N,N-dimethyl-N-hexylamine, perfluoro-N-butylmorpholine, perfluoro-4-(N,N-dimethyl-2-aminoethyl)-morpholine, and F-tertbutylperfluorocyclohexane, or combinations thereof.

Figure 5:
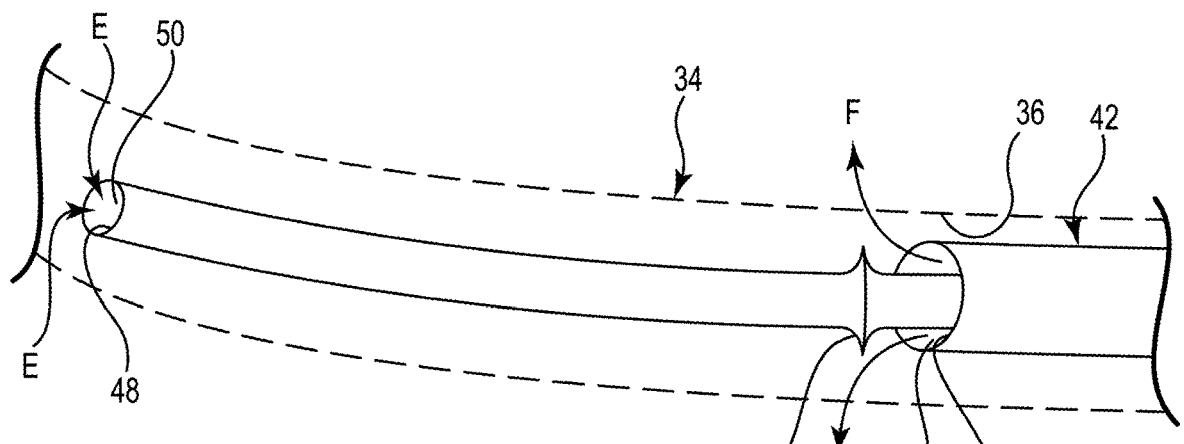
FIG. 5 is a side schematic view of a portion of the system of FIGS. 4A and 4B, according to some embodiments of this disclosure.

Periodically, the insulin-producing cells may need to be replenished. FIG. 5 is a side schematic view of a portion of the system 38 for cell implantation according to another embodiment. In the embodiment shown in FIG. 5, the first external catheter 40 of FIGS. 4A and 4B is replaced with a first external catheter 42 which may be used to replenish insulin-producing cells while the cell encapsulation device 10 remains implanted within the patient. The first external catheter 42 may include a first lumen 44 including a first lumen opening 46, and a second lumen 48 including a second lumen opening 50. The first lumen opening 46 is spaced apart from the second lumen opening 50 along the guide tube 34. The first lumen 44 may be connected to a source of fluid and/or insulin-producing cells. The second lumen 48 may be connect to a vacuum source.

In use, the first external catheter 42 may be inserted into the guide tube 34 at the first access port 20 (FIGS. 4A and 4B), and then moved through the guide tube 34, passing each of the cell channels 30 along the way. At each of the cell channels 30 along the way, the contents of the cell channel 30 may be removed by an extraction flow E through the porous wall 36 of the guide tube 34 and into the second lumen opening 50 to the vacuum source connected to the second lumen 48. Once the cell contents have been extracted, the flow F of fluid and/or fresh insulin-producing cells may be provided from the first lumen opening 46, through the porous wall 36 of the guide tube 34, and into the cell channels 30 (FIGS. 4A and 4B).

Once the contents of the cell channel 30 have been extracted, the cell channel 30 may be filled with a fluid to clean the interior of the cell channel 30, and then the washing fluid extracted. The extract/fill process may be repeated as necessary to clean the cell channels 30 before filling with insulin-producing cells.

In the embodiment shown in FIG. 5, the second lumen 48 is disposed coaxially with the first lumen 44, and the first external catheter 42 further includes a flange 52 disposed between the first lumen opening 46 and the second lumen opening 50. The flange 52 projects outward toward the guide tube 34 to deflect the flow F dispensed from the first lumen 44 toward the porous wall 36 of the guide tube 34 to enhance the flow F through the guide tube 34 and into the cell channels 30.

Figure 6:
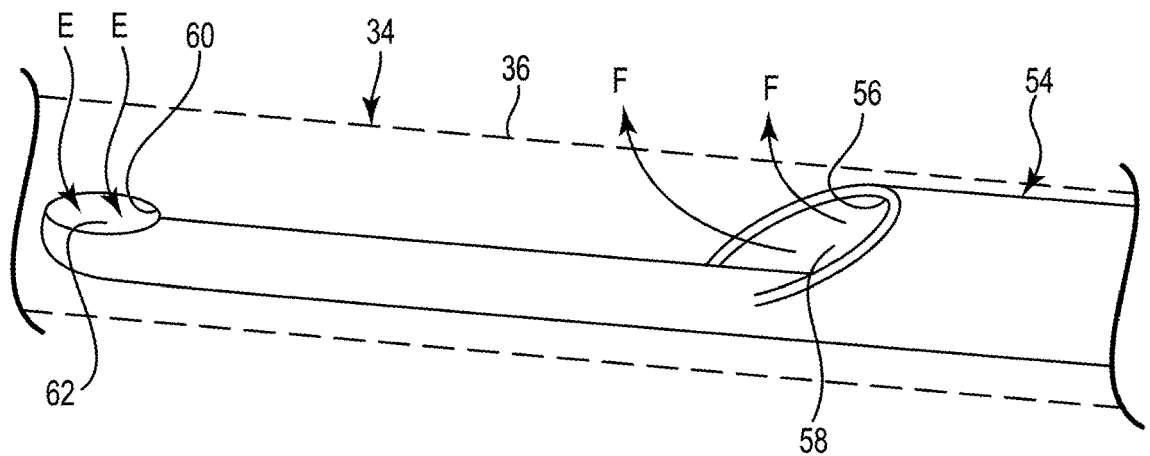
FIG. 6 is a side schematic view of a portion of the system of FIGS. 4A and 4B, according to yet another embodiment of this disclosure.

FIG. 6 is a side schematic view of a portion of the system 38 for cell implantation according to yet another embodiment. In the embodiment shown in FIG. 6, the first external catheter 40 of FIGS. 4A and 4B is replaced with a first external catheter 54 which may be used to replenish insulin-producing cells while the cell encapsulation device 10 remains implanted within the patient. The first external catheter 54 may include a first lumen 56 including a first lumen opening 58, and a second lumen 60 including a second lumen opening 62. The first lumen opening 58 is spaced apart from the second lumen opening 62 along the guide tube 34. The first lumen 56 may be connected to a source of fluid and/or insulin-producing cells. The second lumen 60 may be connect to a vacuum source. The first lumen opening 58 and the second lumen opening 62 may be angled toward the guide tube 34 as shown in FIG. 6 to enhance the extraction flow E and the flow F of fluid through the porous wall 36 of the guide tube 34. The first external catheter 54 may be used as described above for the first external catheter 42 in reference to FIG. 5.

Figure 7:
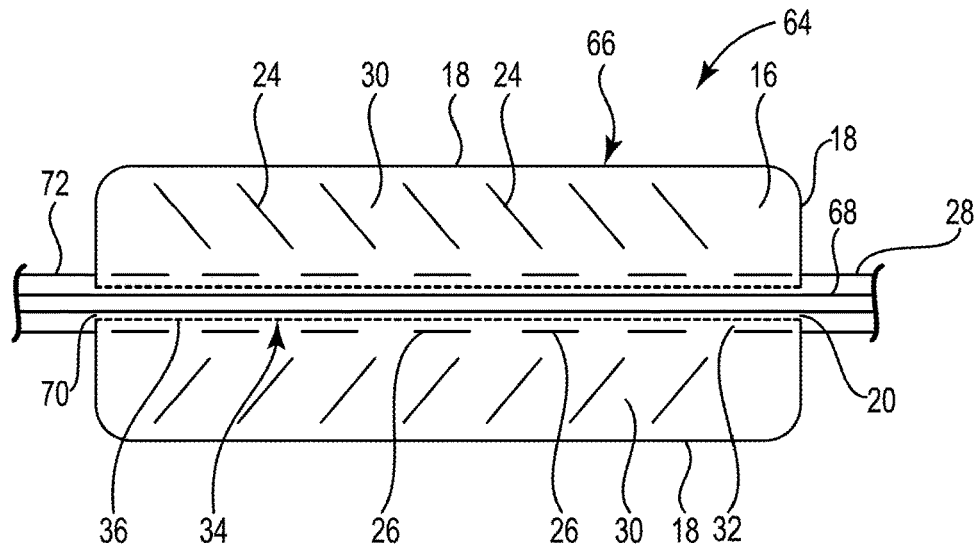
FIG. 7 is a schematic sectional top view of another system for cell implantation, according to some embodiments of this disclosure.

FIG. 7 is a schematic sectional top view of a system 64 for cell implantation including a cell encapsulation device 66 and a first external catheter 68. The cell encapsulation device 66 may be similar to the cell encapsulation device 10 described above, except that the cell encapsulation device 66 may include a second access port 70 and a second access catheter 72. The FIG. 7 is shown with the first membrane 14 removed such that the second membrane 16 is shown for clarity. As shown in FIG. 7, the second access catheter 72 is fluidly connected to the second access port 70 and extends away from the chamber 22 from the second access port 70. The guide tube 34 extends through the chamber 22 from the first access port 20 to the second access port 70. The second access catheter 72 may be a tubular structure as described above in reference to the first access catheter 28. The first external catheter 68 is capable of passing into the chamber 22 through the first access catheter 28, through the guide tube 34, and out of the chamber 22 through the second access catheter 72.

Should vascularization of the cell encapsulation device 66 be insufficient to support the insulin-containing cells within, the first external catheter 68 may be a thin-walled silicone tube though which gasses, such as oxygen and carbon dioxide, may pass. In use, an oxygen-containing fluid such as any of the perfluorocarbon liquid disclosed above, may flow through the first external catheter 68 to provide an oxygenation circuit for the insulin-producing cells within the cell channels 30. Oxygen from the oxygen-containing liquid may diffuse out of the first external catheter 68, through the porous wall 36 of the guide tube 34, and into the cell channels 30 where it may be taken up by the insulin-producing cells. Wastes from the insulin-producing cells may flow in the opposite direction, and be removed as the oxygen-containing fluid flows out of the chamber 22 through the first external catheter 68. Alternatively, the oxygen-containing fluid may be a bodily fluid which may be collected in the peritoneum, and then pumped through the first external catheter 68 to provide oxygen and collect wastes from the insulin-producing cells.

The first external catheter 68 may additionally or alternatively be very elastic and the flow of the oxygen-containing fluid through the first external catheter 68 may be accomplished with a peristaltic movement, providing a pressure pulse that propagates into and through the cell channels 30. The pressure pulse may provide a convective flow in the cell channels 30 to enhance the flow of oxygen and wastes to and from the insulin-producing cells. Once vascularization of the of the cell encapsulation device 66 is sufficient to support the insulin-containing cells within, the first external catheter 68 may be removed from the cell encapsulation device 66.

Figure 8:
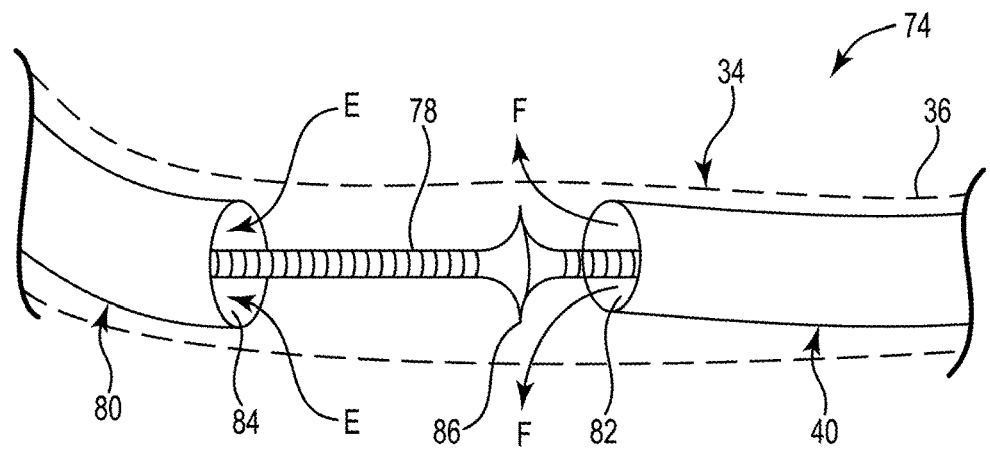
FIG. 8 is a side schematic view of a portion of yet another system for cell implantation, according to some embodiments of this disclosure.

FIG. 8 is a side schematic view of a portion of a system 74 for cell implantation according to another embodiment. System 74 is similar to system 64 described above in reference to FIG. 7, except that the first external catheter 68 is replaced by the first external catheter 40 as described above in reference to FIGS. 4A and 4B, and the system further includes a guide wire 78 and, optionally, a second external catheter 80. As shown in FIG. 8, the, first external catheter 40 includes a first lumen 82 fluidly connected to, for example, a source of fluid or insulin-producing cells outside the patient, as described above in reference to FIGS. 4A and 4B. The second external catheter 80 may include a second lumen 84 connected to a vacuum source. The guide wire 78 may be a guide wire as known in the art.

In use, guide wire 78 may be inserted into the first access catheter 28, through the guide tube 34, and out through the second access catheter 72. The first external catheter 40 may be threaded onto an end of the guide wire 78 and inserted into the first access catheter 28, and then into the guide tube 34 at the first access port 20 of the cell encapsulation device 66 (FIG. 7). The second external catheter 80 may be threaded onto an opposite end of the guide wire 78 and inserted into the second access catheter 72, and then into the guide tube 34 at the second access port 70 opposite the first external catheter 40 (FIG. 7). The first external catheter 40 and the second external catheter 80 are spaced apart from each other, but may move together through the guide tube 34, passing each of the cell channels 30 along the way. At each of the cell channels 30 along the way, the contents of the cell channel 30 may be removed by an extraction flow E through the porous wall 36 of the guide tube 34 and into the second lumen 84. Once the cell contents have been extracted, the flow F of fluid and/or fresh insulin-producing cells may be provided from the first lumen 82, through the porous wall 36 of the guide tube 34, and into the cell channels 30 (FIGS. 4A and 4B).

The guide wire 78 may include a flange 86 disposed between the first external catheter 40 and the second external catheter 80. The flange 86 projects outward toward the guide tube 34 to deflect the flow F dispensed from the first lumen 82 toward the porous wall 36 of the guide tube 34 to enhance the flow F through the guide tube 34 and into the cell channels 30.

The second external catheter 80 may be omitted when the extraction flow E may not be necessary, such as when filling the cell encapsulation device 66 for the first time to inflate the cell channels 30, for example.

In the cell encapsulation devices 10 and 66 described above, only a single guide tube 34 is shown within each cell encapsulation layer 12. However, is it understood that embodiments include cell encapsulation devices 10 and 66 including at least one cell encapsulation layer 12 including at least two guide tubes 34 extending into the cell encapsulation chamber 22 at least two first access ports 20, at least two second access ports 70, or any combination thereof. Including a plurality of guide tubes 34 in a single cell encapsulation layer 12 may increase the speed and efficiency with which the cell encapsulation layer 12 may be filled or replenished with insulin-producing cells, for example.

In the cell encapsulation devices 10 and 66 described above, the guide tube 34 is shown in a generally straight configuration within the cell encapsulation layer 12. However, is it understood that embodiments include cell encapsulation devices 10 and 66 in which the guide tube 34 bends within the cell encapsulation layer to accommodate different shapes for the chamber 22, such as a U-shaped chamber 22, for example.

Figure 9:
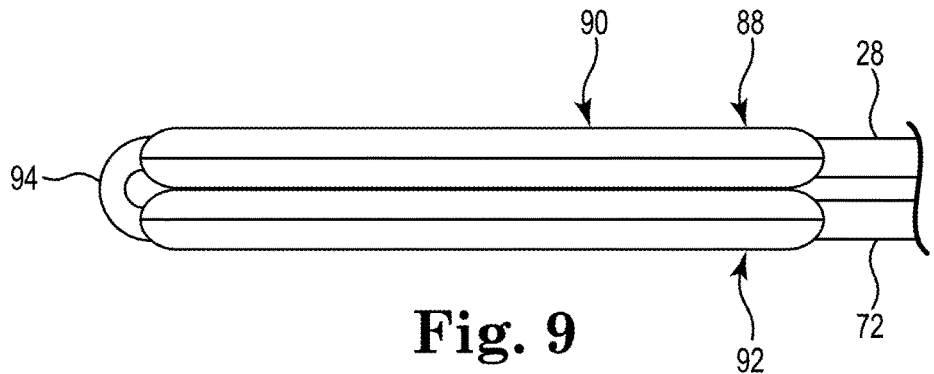
FIG. 9 is a side view of another cell encapsulation device, according to some embodiments of the disclosure.

FIG. 9 is a side view of another cell encapsulation device 88, according to some embodiments of the disclosure. The cell encapsulation device 88 includes two cell encapsulation layers, a first cell encapsulation layer 90 and a second cell encapsulation layer 92. The first cell encapsulation layer 90 and the second cell encapsulation layer 92 may each be similar to those in the cell encapsulation device 66 described above in reference to FIG. 7, except that the second access catheter 72 of the first cell encapsulation layer 90 and the first access catheter 28 of the second cell encapsulation layer 92 may be fluidly connected to form an interlayer catheter 94 fluidly connecting the first cell encapsulation layer 90 to the second cell encapsulation layer 92. The first access catheter 28 of the first cell encapsulation layer 90 and the second access catheter 72 of the second cell encapsulation layer 92 may each extend outside of the patient, or may connect to a subcutaneous injection port 100 (FIG. 11 below) beneath the patient's skin.

Figure 10:
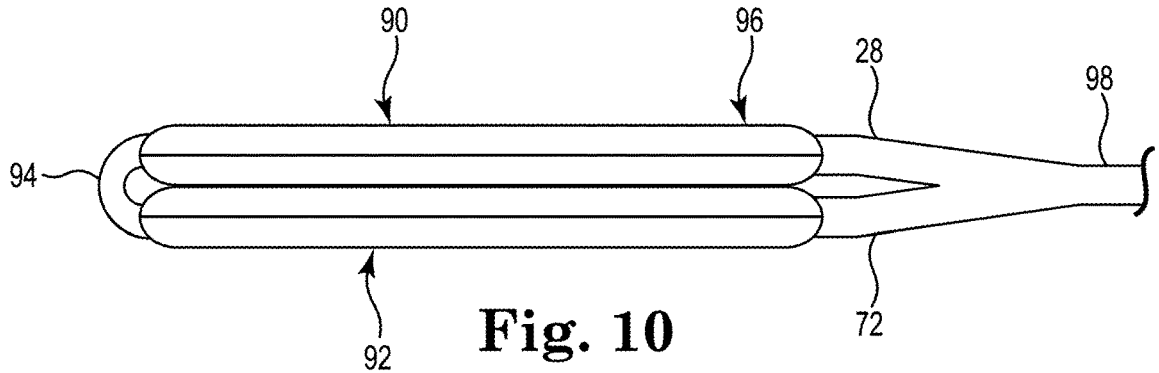
FIG. 10 is a side view of yet another cell encapsulation device, according to some embodiments of the disclosure.

FIG. 10 is a side view of another cell encapsulation device 96, according to some embodiments of the disclosure. The cell encapsulation device 96 is similar to the cell encapsulation device 88 described above, further including a multi-guide tube access catheter 98. The multi-guide tube access catheter 98 may be a single catheter that splits to fluidly connect to the guide tubes 34 in the first cell encapsulation layer 90 and in the second cell encapsulation layer 92. In use, the first external catheter 40 (or any of the other first external catheters or second external catheters described above) may be inserted into the multi-guide tube access catheter 98, and then directed as necessary to either of the guide tubes 34 in first cell encapsulation layer 90 or the second cell encapsulation layer 92. The multi-guide tube access catheter 98 may extend outside of the patient, or may connect to a subcutaneous injection port 100 (FIG. 11 below) beneath the patient's skin. In this way, the number of external or subcutaneous injection ports for the cell encapsulation device may be reduced. Limiting the number of external or subcutaneous injection ports may reduce the opportunities for interaction between the insulin-producing cells in the cell encapsulation device 88 and the patient's immune system.

While only two cell encapsulation layers 90 and 92 are shown in FIGS. 9 and 10, it is understood that the disclosed structure may be extended to embodiments including cell encapsulation devices having as many cell encapsulation layers as necessary to provide the insulin-producing cell capacity required by the patient.

Figure 11:
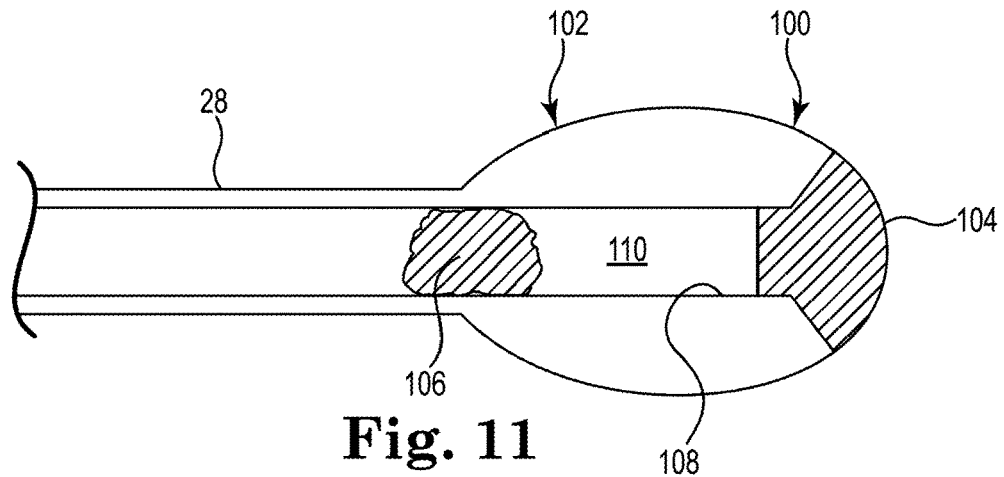
FIG. 11 is a schematic longitudinal cross-sectional view of a portion of a cell encapsulation device including a subcutaneous injection port, according to embodiments of this disclosure.

FIG. 11 is a schematic longitudinal cross-sectional view of a portion of any of the cell encapsulation devices 10, 66, 88, or 96 described above illustrating a subcutaneous injection port 100 connected to an end of the first access catheter 28 opposite the chamber 22 (see e.g. FIG. 1). The subcutaneous injection port 100 may include a port housing 102, and outer septum 104, an inner septum 106. The port housing 102 may include a port lumen 108. The port lumen 108 may extend through the port housing 102 with an end of the port lumen 108 nearest the first access catheter 28 in fluid communication with the first access catheter 28. The outer septum 104 extends across and seals the port lumen 108. The inner septum 106 also extends across and seals the port lumen 108. The inner septum 106 is spaced apart from the outer septum 104 to form a space 110 within the port lumen 108 between the inner septum 106 and the outer septum 104. The inner septum 106 is disposed between the outer septum 104 and the first access catheter 28. The outer septum 104 and the inner septum 106 may be formed of a resilient polymer capable of being penetrated by a tubular needle and of then sealing around the tubular needle. The port housing 102, the outer septum 104 and the inner septum 106 may be formed of a polymer, such as polysiloxane or polycarbonate polyurethane, for example.

Although FIG. 11 is illustrated with the subcutaneous injection port 100 connected the first access catheter 28, it is understood that embodiments include cell encapsulation devices having subcutaneous injection ports like the subcutaneous injection port 100 connected to other access catheters, such as the second access catheter 72 or the multi-guide tube access catheter 98 described above.

Figure 12A:
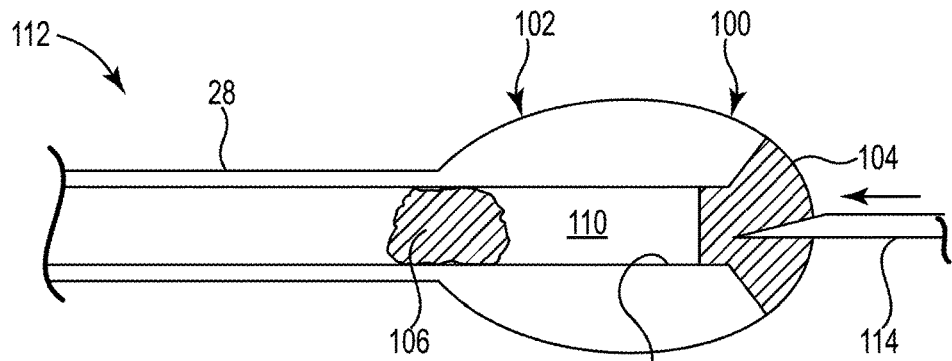
FIGS. 12A-12D are schematic longitudinal cross-sectional views of a portion of another system for cell encapsulation, according to some embodiments of this disclosure.
Figure 12B:
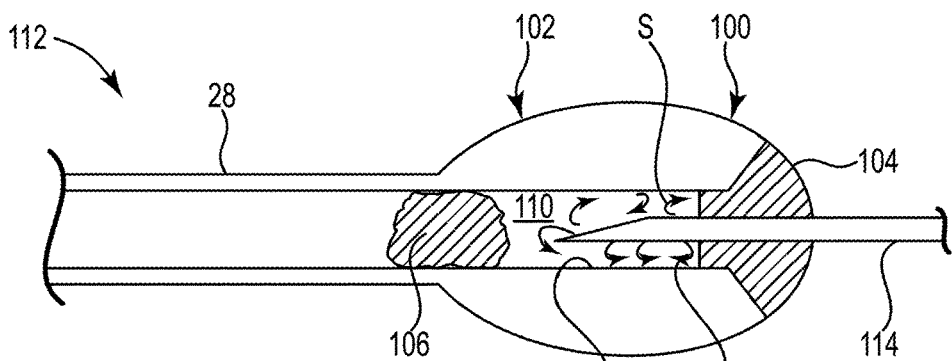
Figure 12C:
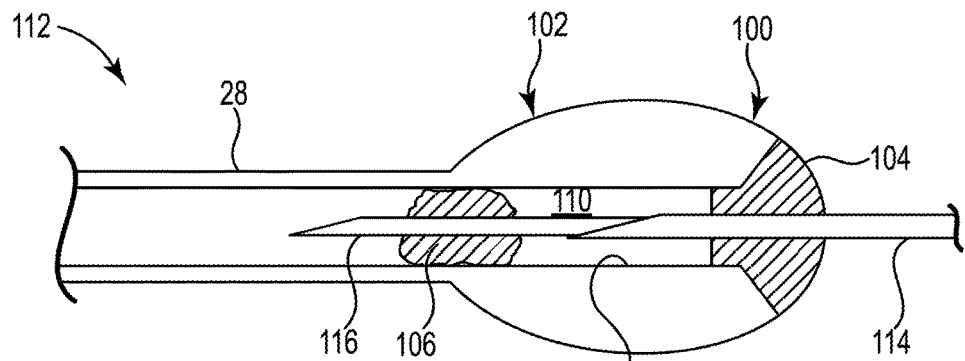
Figure 12D:
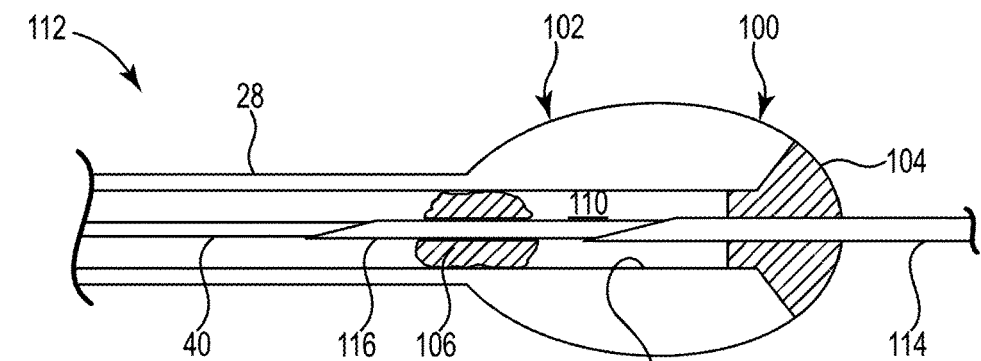

FIGS. 12A-12D are schematic longitudinal cross-sectional views of a portion of another system 112 for cell encapsulation, according to some embodiments of this disclosure. The system 112 may be similar to any of the systems described herein, except that any of the cell encapsulation devices 10, 66, 88, or 96 described above further include the subcutaneous injection port 100 as described above in reference to FIG. 11, and the system 112 may further include an outer tubular needle 114 as shown in FIGS. 12A-12D and an inner tubular needle 116 as shown in FIGS. 12C and 12D. The outer tubular needle 114 is capable of penetrating the outer septum 104 with the outer septum 104 sealing around the outer tubular needle 114. The inner tubular needle 116 is capable of passing through the outer tubular needle 114 and penetrating the inner septum 106 with the inner septum 106 sealing around the inner tubular needle 116.

As shown in FIGS. 12A and 12B, in use, the outer tubular needle 114 may penetrate the skin of the patient (not shown) to reach the subcutaneous injection port 100, and then penetrate the outer septum 104 such that an end of the outer tubular needle 114 is in fluid contact with the space 110 within the port lumen 108 between the outer septum 104 and the inner septum 106. In penetrating the outer septum 104, some bodily fluids may be carried along with the outer tubular needle 114 and into the space 110. The bodily fluids may contain body cells which must remain isolated from the insulin-producing cells within the chamber 22 (FIG. 1). To maintain this isolation, another end (not shown) of the outer tubular needle 114 may be fluidly connected to a source (not shown) of sterilizing fluid S. The sterilizing fluid S may be glutaraldehyde or ethanol, for example. As shown in FIG. 12B, the sterilizing fluid S may be injected through the outer tubular needle 114 and into the space 110 to sterilize the walls of the space 110 and the exposed surfaces of the outer tubular needle 114, destroying any body cells within the space 110.

Once the space 110 is sterilized, the inner tubular needle 116 may pass through the outer tubular needle 114, through the sterilized space 110, and then penetrate the inner septum 106 such that an end of the inner septum 106 is in fluid contact with the first access catheter 28, as shown in FIG. 12C. The first external catheter 40 may then be inserted into another end (not shown) of the inner tubular needle 116 and pass through the inner tubular needle 116, into the first access catheter 28, as shown in FIG. 12D and into the guide tube 34, as described above in reference to FIG. 4A. In this way, the insulin-producing cells may be injected into the cell encapsulation device while maintaining isolation from body cells.

Stop edges (not shown) may be added to proximal ends of the outer tubular needle 114 and the inner tubular needle 116 to prevent the outer tubular needle 114 from penetrating the inner septum 106 and to prevent the inner tubular needle 116 from penetrating too far into the first access catheter 28 and risk puncturing the first access catheter 28, the guide tube 34, the first membrane 14 or the second membrane 16.

Withdrawing the first external catheter 40 while maintaining isolation may be done using the opposite method. The first external catheter 40 may be withdrawn through the inner tubular needle 116, and then the inner tubular needle 116 withdrawn from the first access catheter 28 through the inner septum 106. The inner septum 106 may be formed of a polymer that may seal the hole created by the inner tubular needle 116 when penetrating the inner septum 106. Additionally, or alternatively, the hole may be sealed with an alginate gel, a silicone polymer, or another biocompatible adhesive applied through the inner tubular needle 116 as it withdraws through the inner septum 106. As the inner tubular needle 116 withdraws through the inner septum 106, insulin-producing cells may be carried along with the inner tubular needle 116 into the space 110. To maintain isolation between the insulin-producing cells and the body, the sterilizing fluid S may again be injected through the outer tubular needle 114 and into the space 110 to sterilize the walls of the space 110 and the exposed surfaces of the outer tubular needle 114, destroying any insulin-producing cells within the space 110 (FIG. 12B).

Once the space 110 is sterilized, the outer tubular needle 114 may be withdrawn from the space 110 through the outer septum 104. The outer septum 104 may be formed of a polymer that may seal the hole created by the outer tubular needle 114 when penetrating the outer septum 104. Additionally, or alternatively, the hole may be sealed with an alginate gel, a silicone polymer, or another biocompatible adhesive applied through the outer tubular needle 114 as it withdraws through the outer septum 104.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

Various modifications and additions may be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cell encapsulation device for implantation in a body, the cell encapsulation device comprising:
   one or more cell encapsulation layers, each of the cell encapsulation layers including:
      a first membrane that is semipermeable;
      a second membrane that is semipermeable;
      a first plurality of weld lines, the second membrane attached to the first membrane by the first plurality of weld lines; the first membrane, the second membrane, and the first plurality of weld lines defining a chamber for encapsulating cells, the chamber including at least one access port;
      a guide tube extending into the chamber from the at least one access port, the guide tube including a porous wall along at least a portion of its length, the guide tube capable of guiding movement of a catheter within the chamber;
      at least one access catheter extending away from the chamber from the at least one access port, the at least one access catheter fluidly connected to the guide tube;
   wherein the at least one access port includes a first access port and a second access port; and
   the at least one access catheter includes a first access catheter fluidly connected the first access port, and a second access catheter fluidly connected to the second access port, wherein the guide tube extends through the chamber from the first access port to the second access port.

2. The cell encapsulation device of claim 1, wherein the one or more cell encapsulation layers includes a first cell encapsulation layer and a second cell encapsulation layer, the second access catheter of the first cell encapsulation layer fluidly connected to the first access catheter of the second cell encapsulation layer to fluidly connect the first cell encapsulation layer to the second cell encapsulation layer.

3. The cell encapsulation device of claim 1, wherein the cell encapsulation device further includes an injection port fluidly connected to an end of the at least one access catheter opposite the chamber, the injection port including:
- a port housing forming a port lumen extending through the port housing, an end of the port housing nearest the access catheter in fluid communication with the access catheter;
- an outer septum extending across the port lumen and sealing the port lumen; and
- an inner septum extending across the port lumen and sealing the port lumen, the inner septum spaced apart from the outer septum to form a space within the port lumen and between the inner septum and the outer septum, the inner septum disposed between the outer septum and the access catheter, the outer septum and the inner septum formed of a resilient polymer.

4. A system for cell implantation in a body, the system comprising:
- a cell encapsulation device including:
  - one or more cell encapsulation layers, each of the cell encapsulation layers including:
    - a first membrane that is semipermeable;
    - a second membrane that is semipermeable;
    - a first plurality of weld lines, the second membrane attached to the first membrane by the first plurality of weld lines; the first membrane, the second membrane, and the first plurality of weld lines defining a chamber for encapsulating cells, the chamber including at least one access port;
  - a guide tube extending into the chamber from the at least one access port, the guide tube including a porous wall along at least a portion of its length;
  - at least one access catheter extending away from the chamber from the at least one access port, the at least one access catheter fluidly connected to the guide tube; and
- a first external catheter capable of passing through the at least one access catheter and into the guide tube, the guide tube capable of guiding movement of the first external catheter within the chamber;
- wherein the first external catheter includes a first lumen including a first lumen opening and a second lumen including a second lumen opening, the first lumen opening and the second lumen opening spaced apart from each other along the guide tube, the first lumen opening capable of dispensing a fluid through the porous wall of the guide tube and into the chamber and the second lumen opening capable of extracting the fluid from the chamber through the porous wall of the guide tube.

5. The system of claim 4, wherein the second lumen is disposed coaxially with the first lumen, the first external catheter further including a flange disposed between the first lumen opening and the second lumen opening, the flange projecting outward toward the guide tube to deflect fluid dispensed from the first lumen toward the porous wall of the guide tube.

6. The system of claim 4, further including a second external catheter including a second lumen, wherein:
- the first external catheter includes a first lumen;
- the at least one access port includes a first access port and a second access port, the guide tube extending through the chamber from the first access port to the second access port;
- the at least one access catheter includes a first access catheter fluidly connected the first access port, and a second access catheter fluidly connected to the second access port; and
- the first external catheter is capable of passing through the first access catheter and into the guide tube, the second external catheter is capable of passing through the second access catheter and into the guide tube opposite the first external catheter, the first external catheter and the second external catheter are spaced apart from each other within the chamber, the first external catheter is capable of dispersing a fluid through the porous wall of the guide tube and into the chamber, and the second external catheter is capable of extracting the fluid from the chamber through the porous wall of the guide tube.

7. The system of claim 6, further including a guide wire extending through the first lumen and the second lumen, the guide wire including a flange projecting toward the guide tube between the first external catheter and the second external catheter to deflect fluid dispensed from the first external catheter toward the porous wall of the guide tube.

8. The system of claim 4, wherein the at least one access port includes a first access port and a second access port; and the at least one access catheter includes a first access catheter fluidly connected to the first access port, and a second access catheter fluidly connected to the second access port, the guide tube extending through the chamber from the first access port to the second access port, the first external catheter capable of passing into the chamber through the first access catheter, through the guide tube, and out of the chamber through the second access catheter.

9. The system of claim 4, wherein the cell encapsulation device further includes:
- an injection port fluidly connected to an end of the at least one access catheter opposite the chamber, the injection port including:
  - a port housing forming a port lumen extending through the port housing, an end of the port housing nearest the access catheter in fluid communication with the access catheter;
  - an outer septum extending across the port lumen and sealing the port lumen; and
  - an inner septum extending across the port lumen and sealing the port lumen, the inner septum spaced apart from the outer septum to form a space within the port lumen and between the inner septum and the outer septum, the inner septum disposed between the outer septum and the access catheter, the outer septum and the inner septum formed of a resilient polymer.

10. The system of claim 9, further including:
- an outer tubular needle capable of penetrating the outer septum, the outer septum capable of sealing around the outer tubular needle; and
- an inner tubular needle capable of passing through the outer tubular needle and penetrating the inner septum, the inner septum capable of sealing around the inner tubular needle, the first external catheter capable of passing through the inner tubular needle, the at least one access catheter, and into the guide tube.

* * * * *